US012661162B2

(12) United States Patent
Loschinskey

(10) Patent No.: US 12,661,162 B2
(45) Date of Patent: Jun. 23, 2026

(54) METHODS AND DEVICES FOR BONE FRAGMENT FIXATION

(71) Applicant: DePuy Synthes Products, Inc., Raynham, MA (US)

(72) Inventor: Jacob Hunter Loschinskey, Memphis, TN (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 18/787,364

(22) Filed: Jul. 29, 2024

(65) Prior Publication Data

US 2026/0026852 A1 Jan. 29, 2026

(51) Int. Cl.
| *A61B 17/72* | (2006.01) |
| *A61B 17/80* | (2006.01) |
| *A61B 17/84* | (2006.01) |
| *A61B 17/56* | (2006.01) |
| *A61B 17/86* | (2006.01) |

(52) U.S. Cl.
CPC ...... *A61B 17/7291* (2013.01); *A61B 17/8061* (2013.01); *A61B 17/848* (2013.01); *A61B 2017/564* (2013.01); *A61B 17/8685* (2013.01)

(58) Field of Classification Search
CPC ............ A61B 17/8061; A61B 17/7291; A61B 17/848; A61B 17/7233; A61B 2017/564–2017/565
See application file for complete search history.

(56) References Cited

U.S. PATENT DOCUMENTS

| 5,667,510 | A | 9/1997 | Combs |
| 6,248,109 | B1 | 6/2001 | Stoffella |
| 6,689,136 | B2 | 2/2004 | Stoffella |
| 8,231,625 | B2 | 7/2012 | Graham et al. |
| 8,343,152 | B2 | 1/2013 | Gonzalez-Hernandez |
| 8,460,343 | B2 | 6/2013 | Graham |
| 8,556,946 | B2 | 10/2013 | Prandi et al. |

(Continued)

FOREIGN PATENT DOCUMENTS

| CN | 206979560 U | 2/2018 |
| CN | 219147858 U | 6/2023 |

(Continued)

OTHER PUBLICATIONS

International Search Report and Written Opinion dated Oct. 7, 2025, from corresponding International Application No. PCT/IB2025/056864.

*Primary Examiner* — Julianna N Harvey

(57) ABSTRACT

A method for fixating a bone fragment may include delivering a first device into a first bone such that a first portion of the first device is fixed in the first bone and a second portion of the first device extends outward from the first bone; cutting the first bone to generate the bone fragment, wherein the first portion of the first device is fixed in the bone fragment; and placing an apparatus on an exterior surface of the bone fragment, the apparatus having two or more fixation holes, at least one of which includes a slot. The method may include positioning the second portion through the slot; securing the apparatus onto the exterior surface of the bone fragment by delivering a first fixation device into the bone fragment through a second fixation hole; and removing the first device from the first bone.

16 Claims, 19 Drawing Sheets

(56) References Cited

U.S. PATENT DOCUMENTS

| | | | |
|---|---|---|---|
| 8,986,353 | B2 | 3/2015 | Johnson et al. |
| 9,005,255 | B2 | 4/2015 | Lewis et al. |
| 9,060,822 | B2 | 6/2015 | Lewis et al. |
| 9,522,022 | B2 | 12/2016 | Cheney et al. |
| 9,572,607 | B2 | 2/2017 | Johnson et al. |
| 9,888,949 | B2 | 2/2018 | Johnson et al. |
| 9,949,744 | B2 | 4/2018 | McCormick |
| 10,022,170 | B2 | 7/2018 | Leemrijse et al. |
| 10,064,667 | B2 | 9/2018 | Leemrijse et al. |
| 10,213,236 | B2 | 2/2019 | Lewis et al. |
| 10,881,436 | B2 | 1/2021 | Muller et al. |
| 11,020,148 | B2 | 6/2021 | Hollis et al. |
| 2002/0143337 | A1 | 10/2002 | Orbay et al. |
| 2003/0040750 | A1 | 2/2003 | Stoffella |
| 2004/0111090 | A1 | 6/2004 | Dahners |
| 2005/0033302 | A1 | 2/2005 | Frank |
| 2006/0004362 | A1* | 1/2006 | Patterson ........... A61B 17/8057 606/291 |
| 2006/0009770 | A1* | 1/2006 | Speirs ................ A61B 17/8047 606/328 |
| 2008/0015593 | A1 | 1/2008 | Pfefferle et al. |
| 2009/0036931 | A1 | 2/2009 | Pech et al. |
| 2010/0274293 | A1 | 10/2010 | Terrill et al. |
| 2011/0257652 | A1 | 10/2011 | Roman |
| 2012/0016428 | A1 | 1/2012 | White et al. |
| 2012/0065638 | A1 | 3/2012 | Moore |
| 2012/0303033 | A1 | 11/2012 | Weiner et al. |
| 2013/0172942 | A1 | 7/2013 | Lewis et al. |
| 2015/0327900 | A1 | 11/2015 | Toro et al. |
| 2016/0199113 | A1 | 7/2016 | Penzimer |
| 2016/0213384 | A1 | 7/2016 | Fallin et al. |
| 2016/0354127 | A1 | 12/2016 | Lundquist et al. |
| 2017/0049576 | A1 | 2/2017 | Guilford et al. |
| 2017/0164989 | A1* | 6/2017 | Weiner .............. A61B 17/8061 |
| 2017/0172638 | A1 | 6/2017 | Santrock et al. |
| 2017/0196602 | A1* | 7/2017 | Lundquist ......... A61B 17/8061 |
| 2018/0070995 | A1 | 3/2018 | Kay et al. |
| 2018/0161080 | A1 | 6/2018 | Johnson et al. |
| 2018/0214163 | A1 | 8/2018 | McCormick |
| 2019/0125418 | A1 | 5/2019 | Muller et al. |
| 2024/0058041 | A1 | 2/2024 | Lundquist et al. |

FOREIGN PATENT DOCUMENTS

| | | | |
|---|---|---|---|
| EP | 2228026 | B1 | 11/2013 |
| FR | 2878431 | A1 | 6/2006 |
| WO | 2012112642 | A1 | 8/2012 |
| WO | 2017011589 | A1 | 1/2017 |
| WO | 2020041841 | A1 | 3/2020 |

* cited by examiner

100

10

12

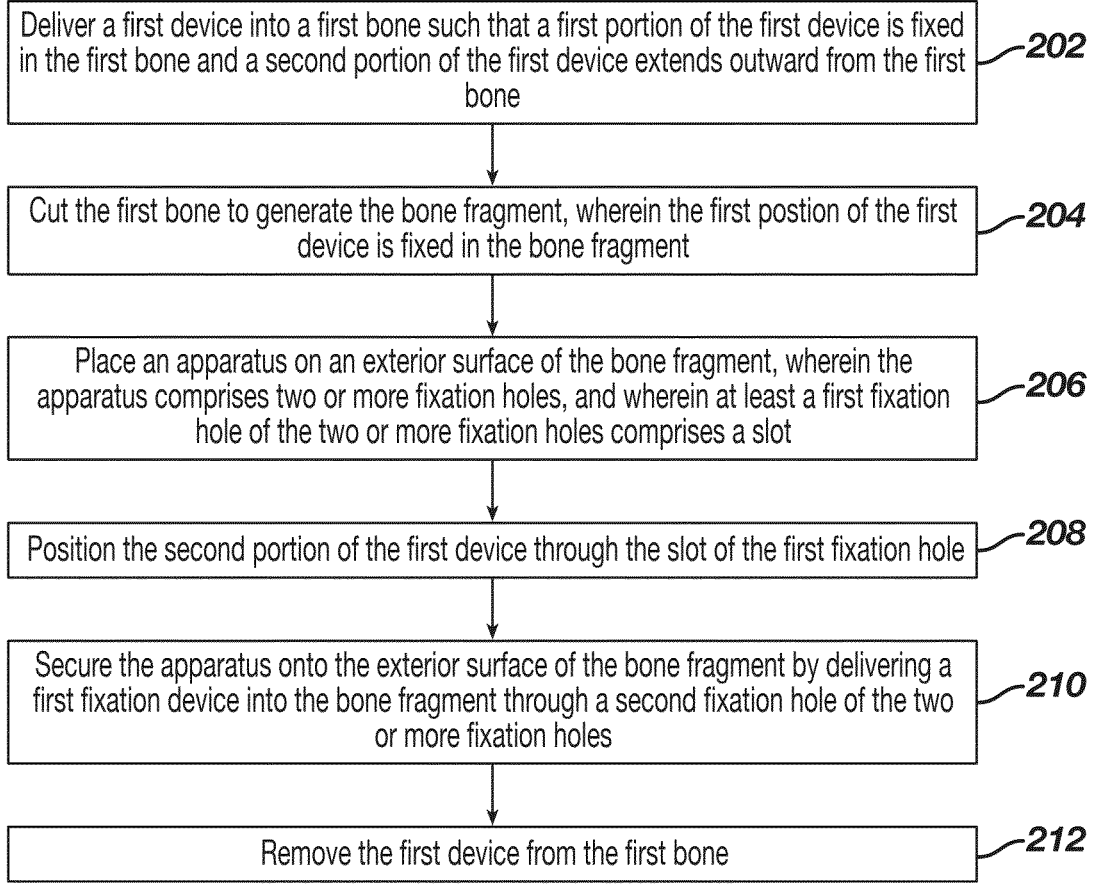

_200_

Deliver a first device into a first bone such that a first portion of the first device is fixed in the first bone and a second portion of the first device extends outward from the first bone ⟋202

Cut the first bone to generate the bone fragment, wherein the first postion of the first device is fixed in the bone fragment ⟋204

Place an apparatus on an exterior surface of the bone fragment, wherein the apparatus comprises two or more fixation holes, and wherein at least a first fixation hole of the two or more fixation holes comprises a slot ⟋206

Position the second portion of the first device through the slot of the first fixation hole ⟋208

Secure the apparatus onto the exterior surface of the bone fragment by delivering a first fixation device into the bone fragment through a second fixation hole of the two or more fixation holes ⟋210

Remove the first device from the first bone ⟋212

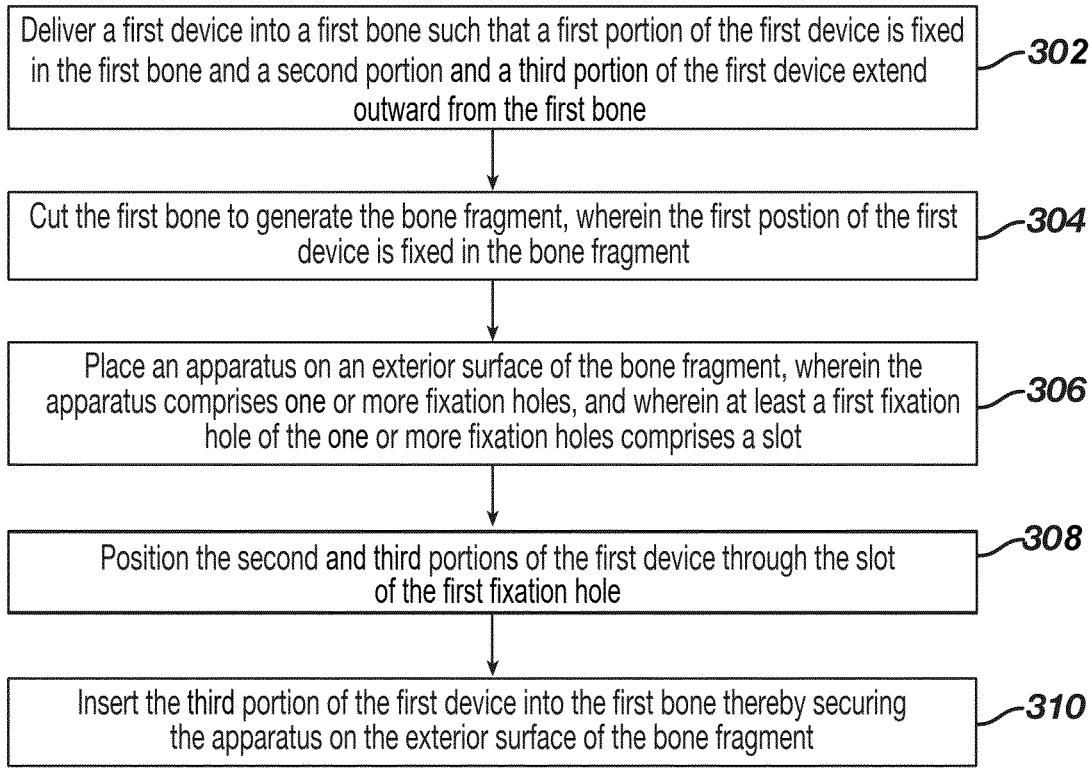

Deliver a first device into a first bone such that a first portion of the first device is fixed in the first bone and a second portion and a third portion of the first device extend outward from the first bone — _302_

Cut the first bone to generate the bone fragment, wherein the first postion of the first device is fixed in the bone fragment — _304_

Place an apparatus on an exterior surface of the bone fragment, wherein the apparatus comprises one or more fixation holes, and wherein at least a first fixation hole of the one or more fixation holes comprises a slot — _306_

Position the second and third portions of the first device through the slot of the first fixation hole — _308_

Insert the third portion of the first device into the first bone thereby securing the apparatus on the exterior surface of the bone fragment — _310_

_FIG. 18_

METHODS AND DEVICES FOR BONE FRAGMENT FIXATION

FIELD

The present disclosure generally relates to methods and devices for bone fragment fixation. More specifically, certain embodiments relate to methods and devices for fixation of bone fragments in relation to a fixation apparatus and surrounding anatomy.

BACKGROUND

Osteotomies are surgical procedures used to treat various orthopedic conditions and injuries. During these procedures, or others involving fracture repair, a bone (such as in the knee, hip, toe, etc.) can be cut to shorten, lengthen, or change its alignment with respect to the surrounding anatomy. Typical procedures involve securing the bone fragment to some form of implant, which requires a surgeon to manipulate the bone fragment by hand. This process can be challenging as the size of the bone fragment(s) involved in such procedure can be very small.

Accordingly, alternative methods and devices for bone fragment fixation would be useful.

SUMMARY

The present disclosure is directed to apparatus and methods for bone fragment fixation.

An example method is provided for fixating a bone fragment. The method may include delivering a first device into a first bone such that a first portion of the first device is fixed in the first bone and a second portion of the first device extends outward from the first bone. The method may include cutting the first bone to generate the bone fragment, wherein the first portion of the first device is fixed in the bone fragment. The method may include placing an apparatus on an exterior surface of the bone fragment, wherein the apparatus has two or more fixation holes, and wherein at least a first fixation hole of the two or more fixation holes includes a slot. The method may include positioning the second portion of the first device through the slot of the first fixation hole. The method may include securing the apparatus onto the exterior surface of the bone fragment by delivering a first fixation device into the bone fragment through a second fixation hole of the two or more fixation holes. The method may include removing the first device from the first bone.

Another example method is provided for fixating a bone fragment. The method may include delivering a first device into a first bone such that a first portion of the first device is fixed in the first bone and a second portion and a third portion of the first device extend outward from the first bone. The method may include cutting the first bone to generate the bone fragment, wherein the first portion of the first device is fixed in the bone fragment. The method may include placing an apparatus on an exterior surface of the bone fragment, wherein the apparatus has one or more fixation holes, and wherein at least a first fixation hole of the one or more fixation holes includes a slot. The method may include positioning the second and third portions of the first device through the slot of the first fixation hole. After positioning the second and third portions of the first device through the slot of the first fixation hole, the method may include inserting the third portion of the first device into the first bone thereby securing the apparatus on the exterior surface of the bone fragment.

An example apparatus is provided for fixating a bone fragment. The apparatus may include a plate, and one or more fixation holes. A first fixation hole of the one or more fixation holes may include a slot.

BRIEF DESCRIPTION OF THE DRAWINGS

The above and further aspects of this disclosure are further discussed with reference to the following description in conjunction with the accompanying drawings, in which like numerals indicate like structural elements and features in various figures. The drawings are not necessarily to scale, emphasis instead being placed upon illustrating principles of the disclosure. The figures depict one or more implementations of the inventive devices, by way of example only, not by way of limitation.

FIG. 17 is a flowchart of a method for bone fragment fixation, according to aspects of the present disclosure.

FIG. 18 is a flowchart of a method for bone fragment fixation, according to aspects of the present disclosure.

DETAILED DESCRIPTION

The example devices and methods of treatment described herein generally involve providing bone fragment fixation, such as in the hip, knee, foot, or hand. Existing methods of treatment typically require a bone fragment be manipulated by hand to align it properly with surrounding anatomy and to secure it to a fixation apparatus. These existing methods can present challenges given the small size of the involved bone(s) or bone fragment(s). Accordingly, the various example systems and methods presented herein aim to overcome this and other challenges in existing methods of treatment. Features from each example are combinable with other examples as understood by persons skilled in the pertinent art.

Figure 1:
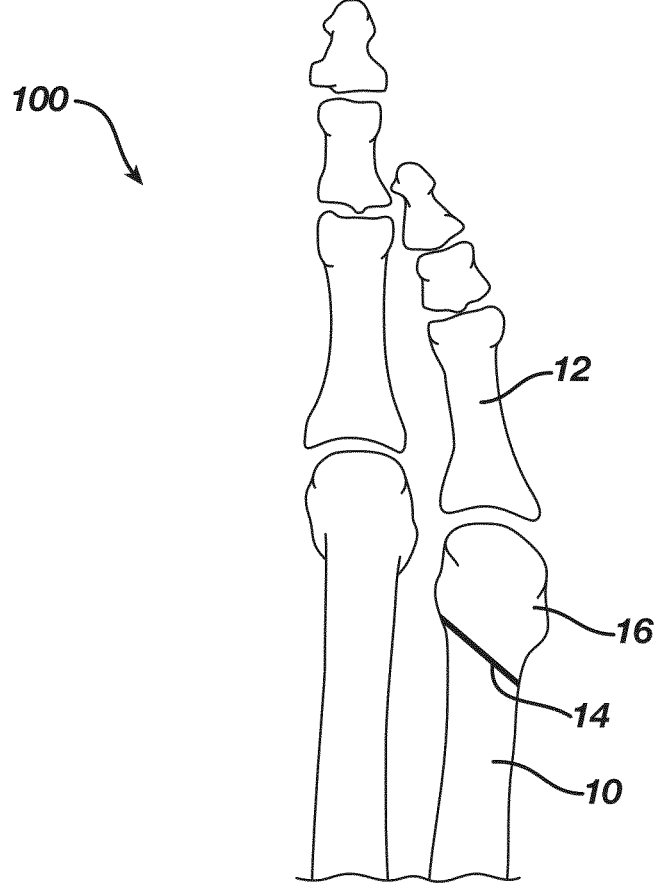
FIG. 1 is an illustration of an example environment for bone fragment fixation, according to aspects of the present disclosure.

FIG. 1 is an illustration of an example environment 100 in which a bone fragment fixation method may take place. The environment 100 may include a first bone 10, such as in a finger, and an adjacent bone 12. As further discussed below, a cut 14 may be made in the first bone 10 thereby generating a bone fragment 16 to which a fixation apparatus might be secured, as further discussed below.

Figure 2:
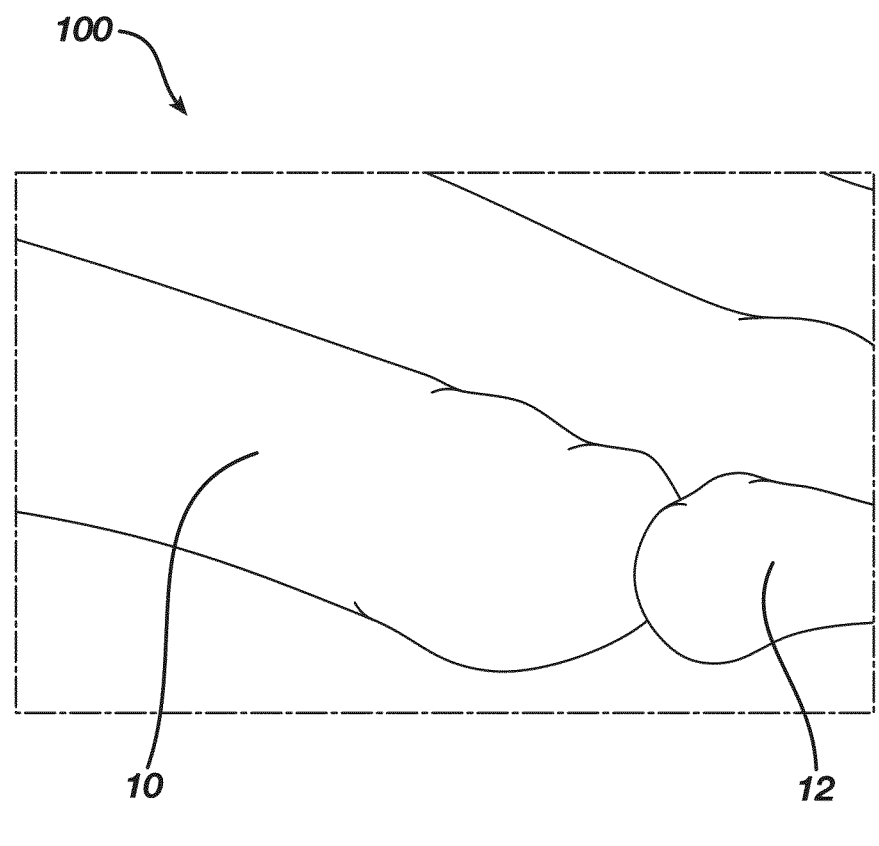
FIG. 2 is an illustration of a step in an example bone fragment fixation method, according to aspects of the present disclosure.

FIGS. 2-9 provide illustrations of a step-by-step process for a method of bone fragment fixation that might take place in example environment 100. FIG. 2 provides a first bone 10 and an adjacent bone 12 in an environment 100. In such example, first bone 10 might require a repair, such as an osteotomy or a bone fragment repair.

Figure 3:
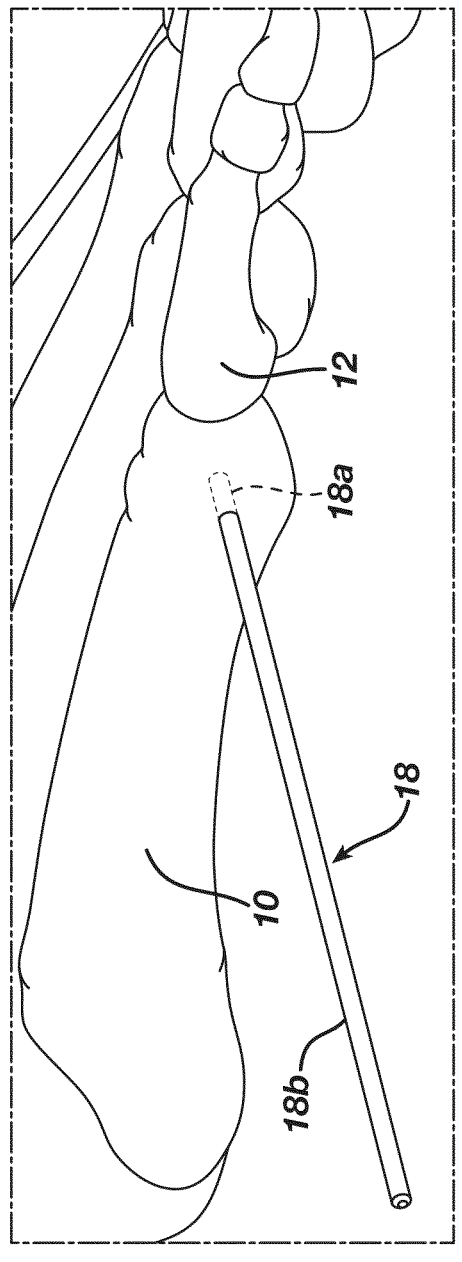
FIG. 3 is an illustration of a step in an example bone fragment fixation method, according to aspects of the present disclosure.

In FIG. 3, a first device 18, such as a Kirschner wire ("K-wire"), may be delivered into the first bone 10 in a specific area where a repair is required. Once delivered, a first portion 18a of the first device 18 may be fixed in the first bone 10, while a second portion 18b of the first device 18 may extend outward from the first bone 10. In some embodiments, as discussed further below with respect to FIGS. 10-12, the first device 18 may be a screw, such as a snap-off screw. In such embodiments, a delivery device may be utilized to deliver the snap-off screw into the first bone 10 such that a first portion of the screw is fixed in the first bone 10, while a second portion and a third portion of the screw extend outward from the first bone 10.

Figure 4:
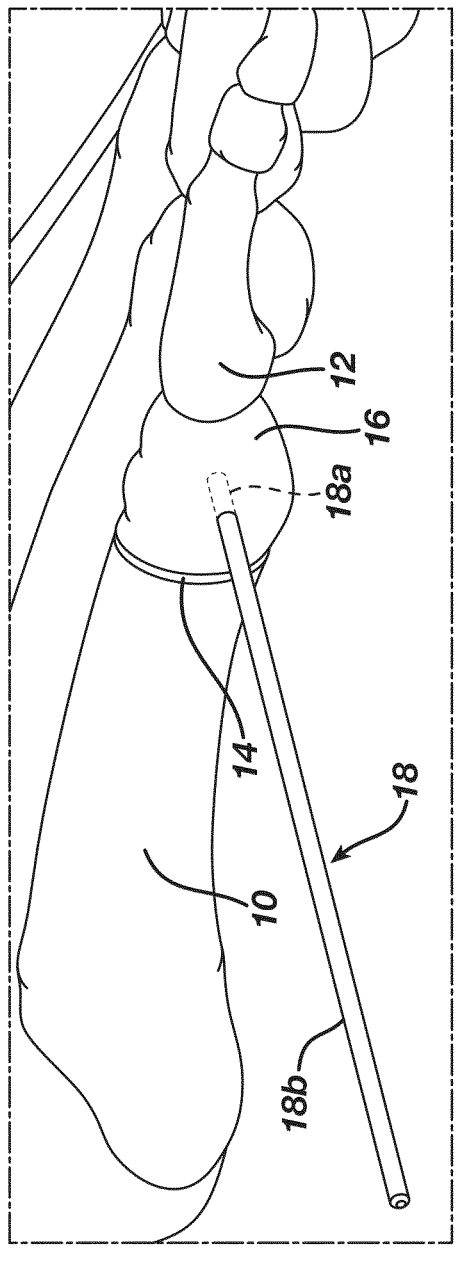
FIG. 4 is an illustration of a step in an example bone fragment fixation method, according to aspects of the present disclosure.

In FIG. 4, a cut 14 is made in the first bone 10 such that the first portion 18a of the first device is fixed in a bone fragment 16 of the first bone 10. An advantage of such procedure is that the first device 18 may then be utilized to aid a surgeon in manipulating the bone fragment 16, as further discussed below.

Figure 5A:
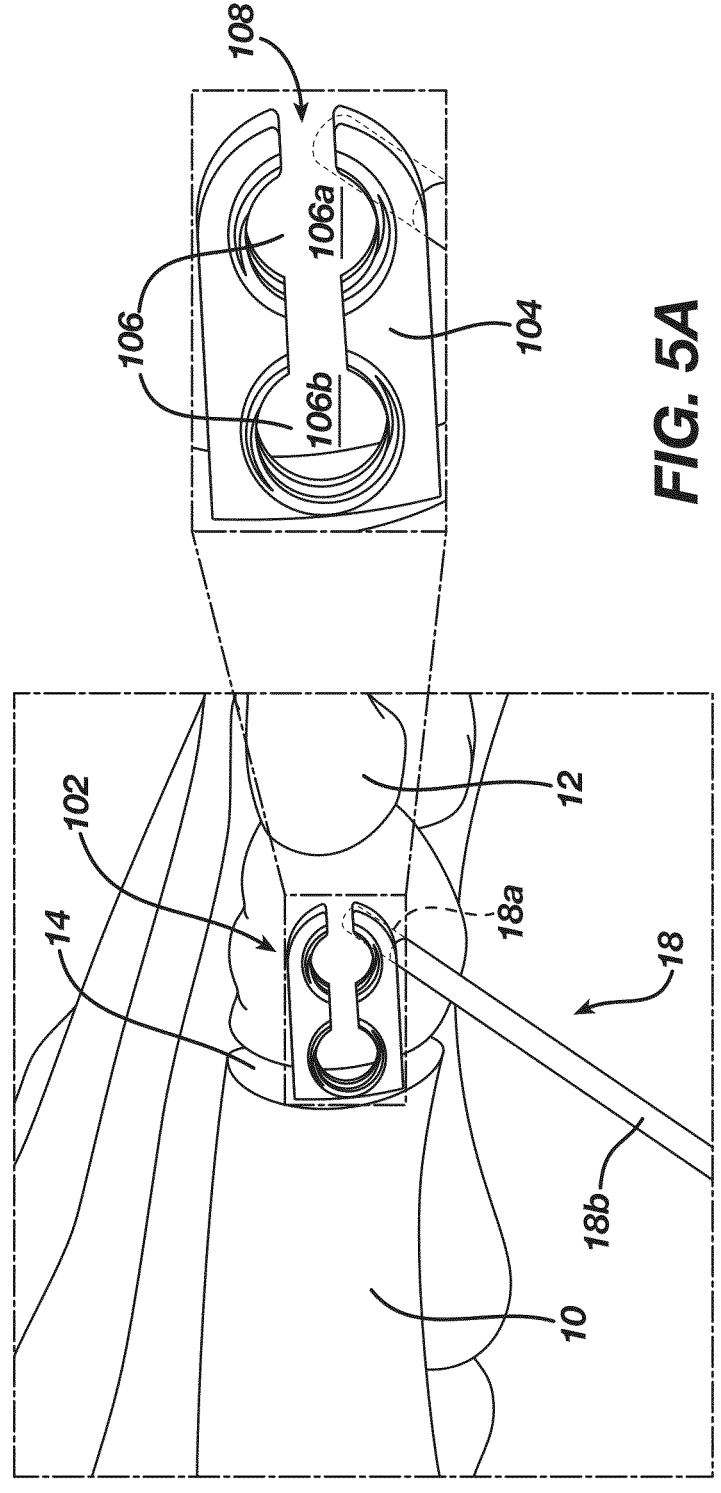
FIG. 5A is an illustration of a step in an example bone fragment fixation method, according to aspects of the present disclosure.
Figure 5B:
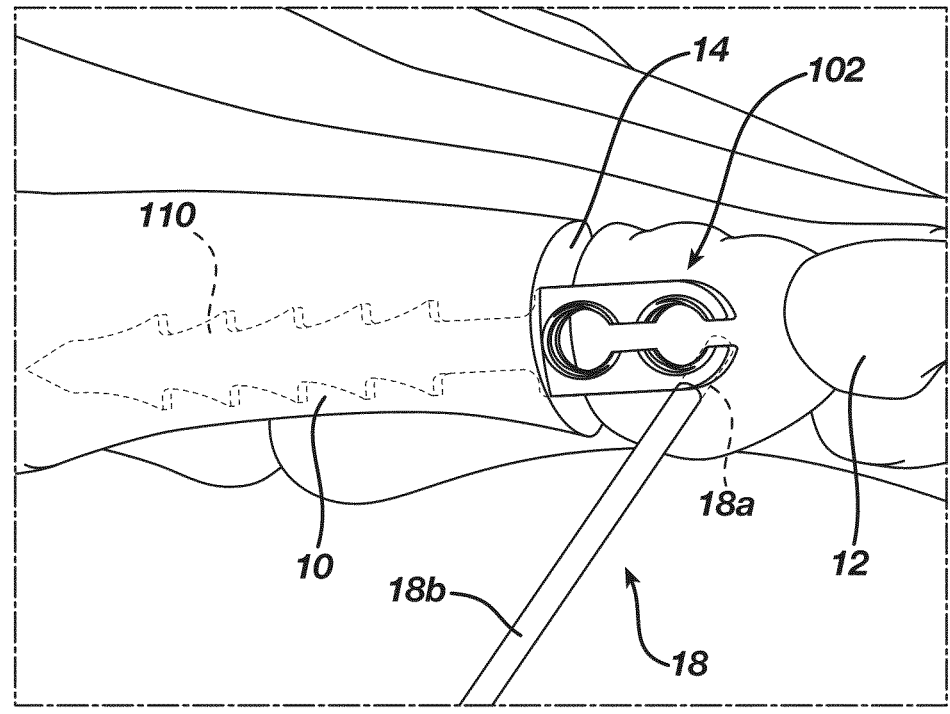
FIG. 5B is an illustration of a step in an example bone fragment fixation method, according to aspects of the present disclosure.

In FIG. 5A, at least a first portion of an apparatus 102 may be placed on an exterior surface of the bone fragment 16. The apparatus 102 may include a plate 104, and two or more fixation holes 106. In some embodiments, the plate 104 may be planar. In some embodiments, the two or more fixation holes 106 may include at least a first fixation hole 106a having a slot 108, as well as one or more second fixation holes 106b fully enclosed within the plate 104. As further discussed below, the slot 108 may be disposed on an end or on a side of the plate 104. In some embodiments, as shown in FIG. 5B and further discussed below with respect to FIGS. 14A-14C, at least a second portion of the apparatus

102, such as an extension 110, may be delivered intramedullary to the first bone 10. Such feature may aid in further securing the apparatus 102 to the first bone 10.

Figure 6:
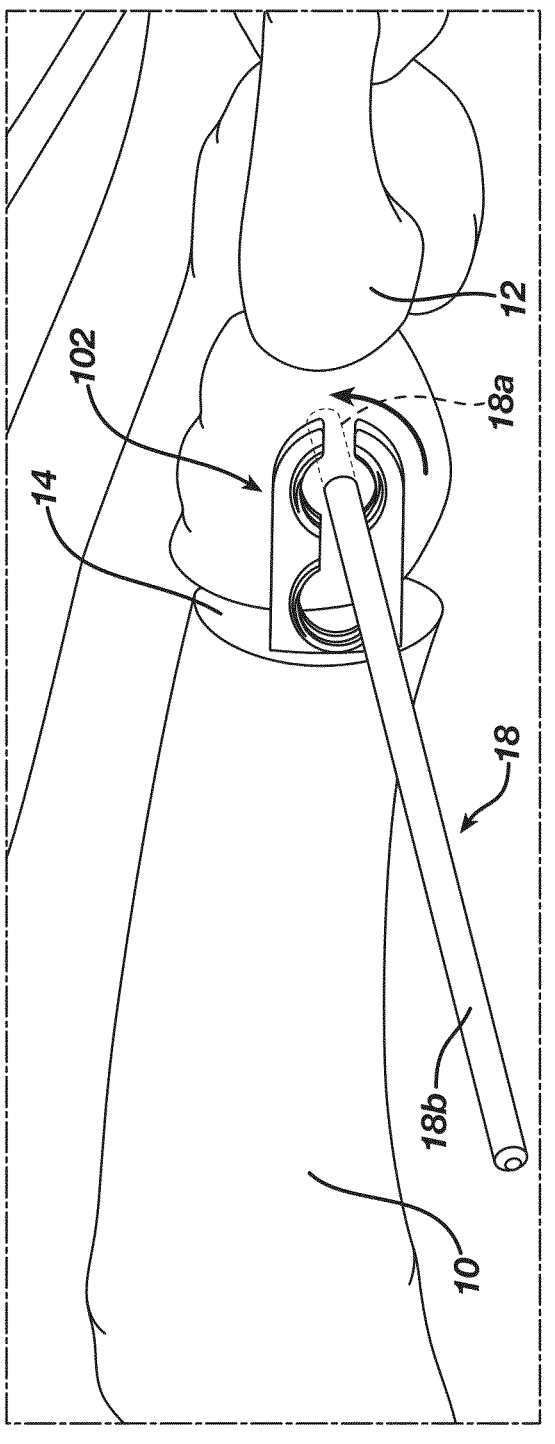
FIG. 6 is an illustration of a step in an example bone fragment fixation method, according to aspects of the present disclosure.

In FIG. 6, a surgeon might hold the second portion 18b of the first device 18 and position the second portion 18b through the slot 108 and into the first fixation hole 106a of the apparatus 102, as indicated by the arrow. This feature may allow the surgeon to align the bone fragment 16 more easily and efficiently with the remaining portion of the first bone 10, the adjacent bone 12, and/or to align the bone fragment 16 to anatomically normal conditions, such as a pre-fracture or pre-injury condition, or a typical anatomical condition for the bone or body part at issue. An advantage of this procedure is that the bone(s) on which the surgeon is operating or manipulating may be very small and as such, the first device 18 may allow the surgeon to manipulate the bone(s) or bone fragment(s) more easily as opposed to an exclusively by-hand method.

Figure 7:
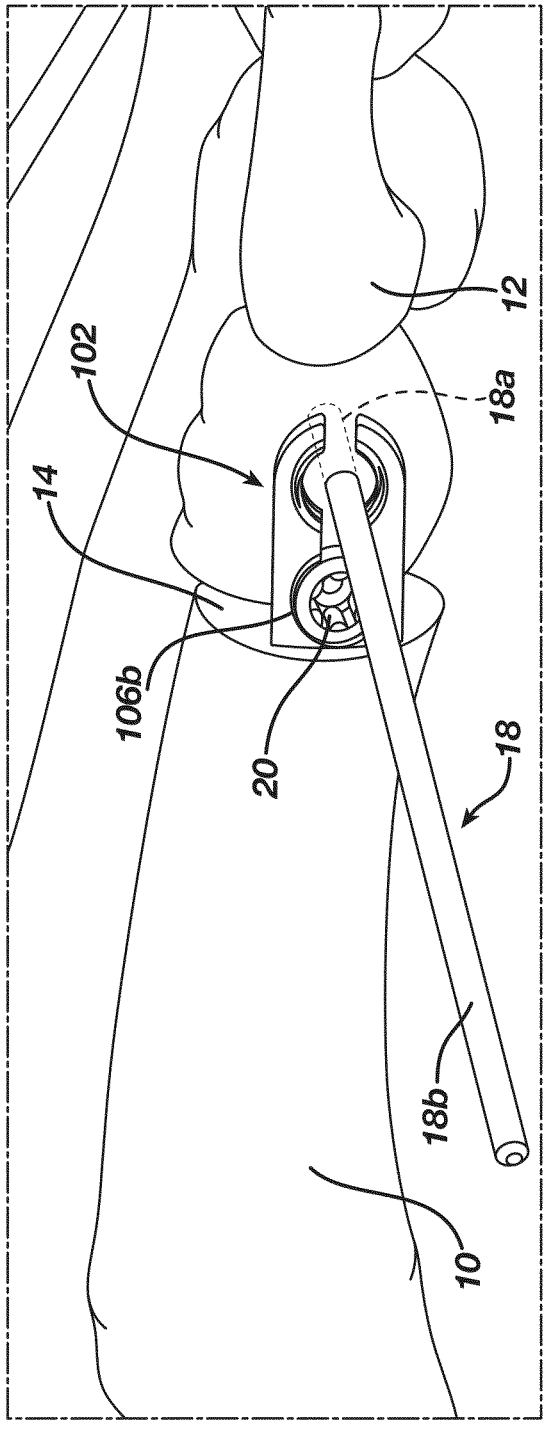
FIG. 7 is an illustration of a step in an example bone fragment fixation method, according to aspects of the present disclosure.

In FIG. 7, a first fixation device 20 (e.g., a screw) may be inserted into a second fixation hole 106b to secure the apparatus 102 to the bone fragment 16.

Figure 8:
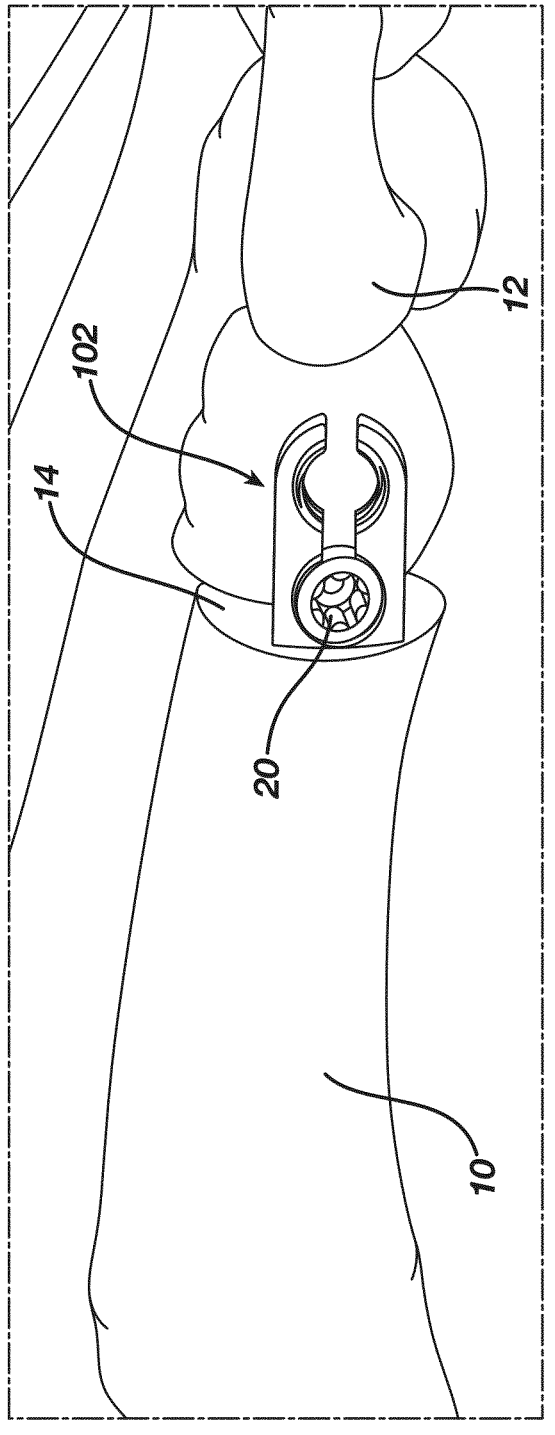
FIG. 8 is an illustration of a step in an example bone fragment fixation method, according to aspects of the present disclosure.

In FIG. 8, the first device 18 may then be removed from the first bone 10.

Figure 9:
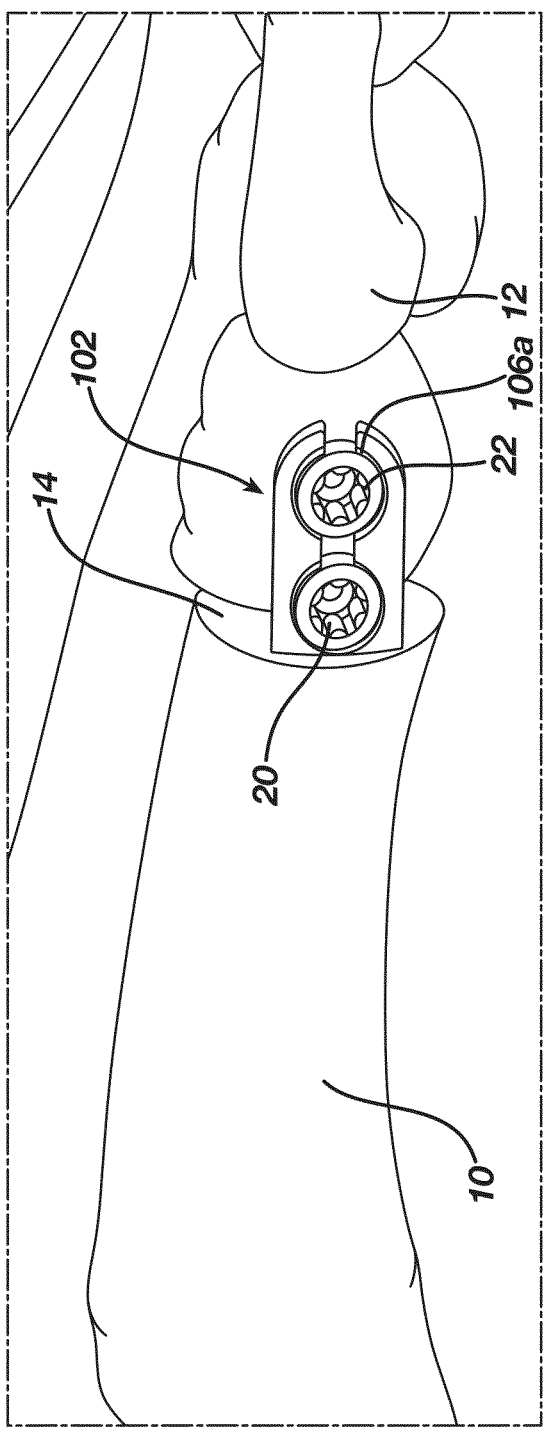
FIG. 9 is an illustration of a step in an example bone fragment fixation method, according to aspects of the present disclosure.

In FIG. 9, a second fixation device 22 (e.g., a screw) may be inserted into the first fixation hole 106a of the apparatus 102. This step may provide for added security of the apparatus 102 onto the first bone 10.

Figure 10:
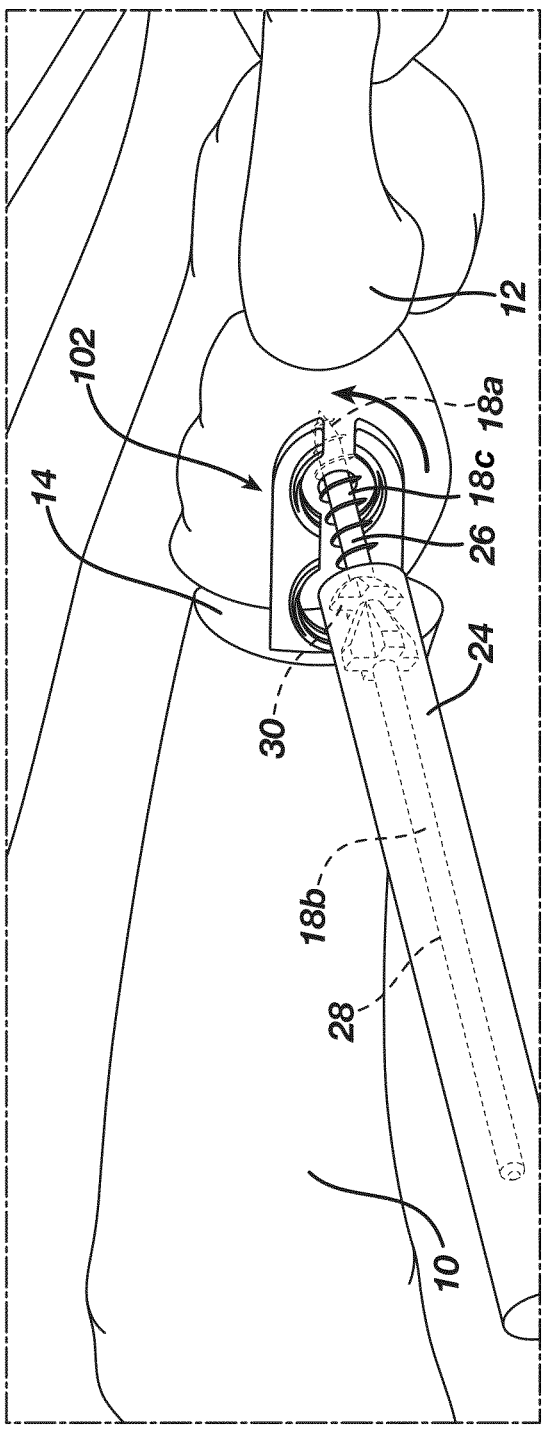
FIG. 10 is an illustration of a step in an example bone fragment fixation method, according to aspects of the present disclosure.
Figure 11:
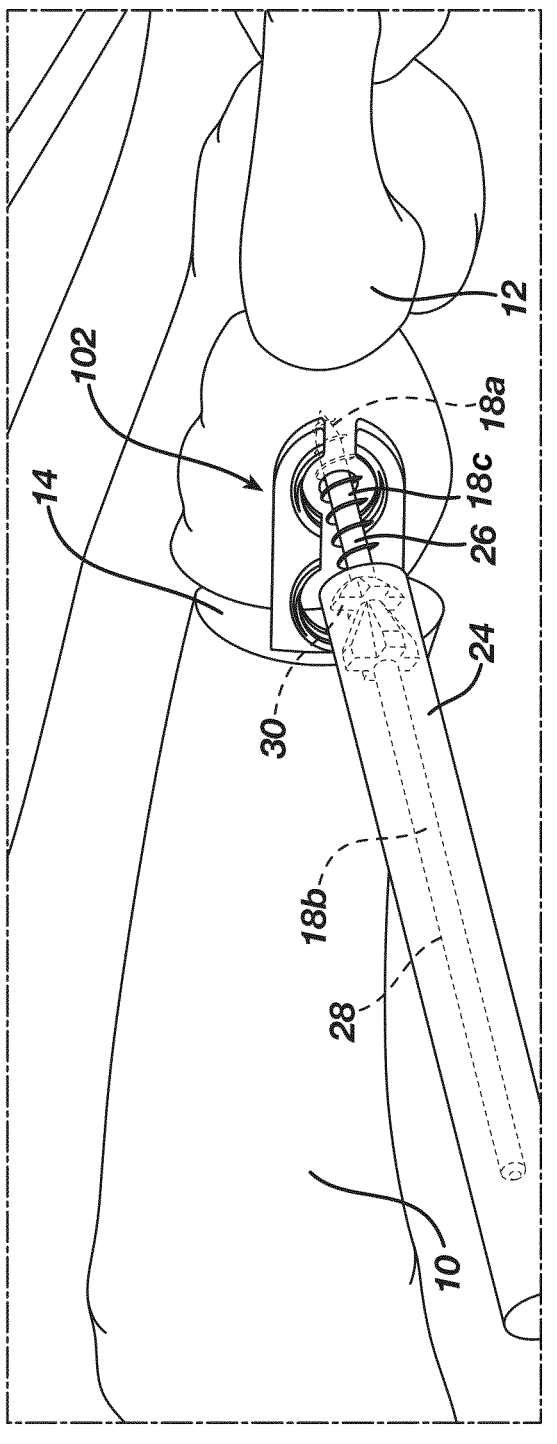
FIG. 11 is an illustration of a step in an example bone fragment fixation method, according to aspects of the present disclosure.
Figure 12:
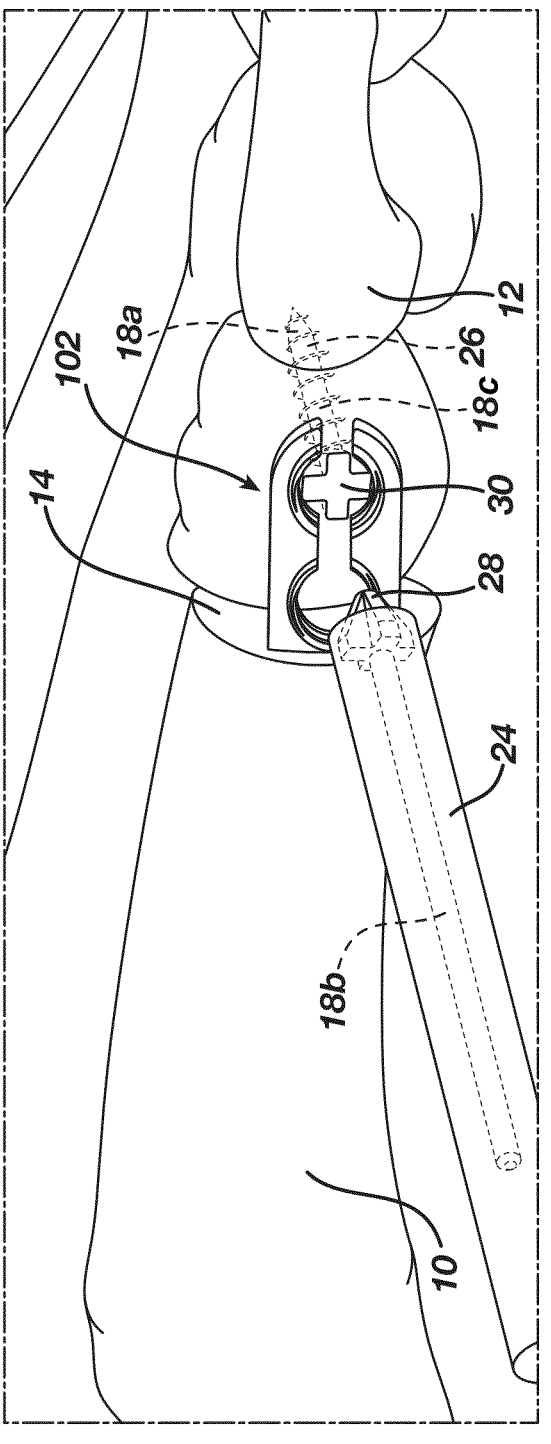
FIG. 12 is an illustration of a step in an example bone fragment fixation method, according to aspects of the present disclosure.

As discussed above, rather than a K-wire, the first device 18 may instead be a snap-off screw. In such embodiment, the first several steps of a bone fragment fixation method may be the same or similar to those illustrated and discussed above with respect to FIGS. 2-6. FIGS. 10-12 show how the remaining method steps might be different in comparison to those illustrated and described above with respect to FIGS. 7-9. That is, as shown in FIGS. 10-11, a delivery device 24 may be used to insert (e.g., screw) the first device 18 into the first bone 10 such that a first portion 18a of the snap-off screw, such as a first section of screw 26, is fixed in the first bone 10 (e.g., the bone fragment 16 after the first bone 10 is cut), while a second portion 18b of the snap-off screw, such as stem 28, and a third portion 18c of the snap-off screw, such as a second section of the screw 26, extend outward from the bone. As particularly shown in FIG. 10, a surgeon might hold the delivery device 24, which houses the second portion 18b of the first device 18, to position the connected second and third portions 18b, 18c through the slot 108 and into the first fixation hole 106a of the apparatus 102, as indicated by the arrow. Once positioned in such fashion (FIG. 11), the first device 18 is ready to be further delivered into the bone fragment 16.

As shown in FIG. 12, rather than insert first fixation device 20 into the second fixation hole 106b, as in FIG. 7 above, using a snap-off screw as the first device 18 provides for the snap-off screw acting as both the first device 18 and the first fixation device 20. That is, once the surgeon has positioned the snap-off screw through the slot 108 and into the first fixation hole 106a, the screw can be further delivered into the bone fragment 16 such that both the first and third portions 18a, 18c of the first device 18 are screwed into the bone fragment 16. The snap-off screw may be screwed into the bone until a screw head 30 of the screw is flush with an exterior surface of the first bone 10. Once the snap-off screw is in proper position, the delivery device 24 can be removed while "snapping off" the second portion 18b of the first device 18 from the screw head 30. In this scenario, the snap-off screw acts as the first fixation device 20 securing the apparatus 102 to the bone fragment 16. In some embodiments, a second fixation device (e.g., a screw) may then be inserted into a second fixation hole 106b to further secure the apparatus 102 onto the first bone 10.

Figure 13A:
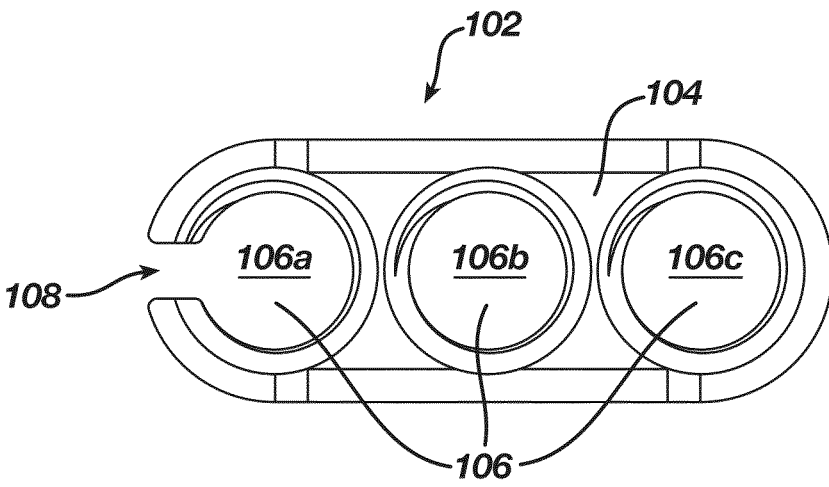
FIGS. 13A-13C provide top (A), end (B), and side (C) views of an example apparatus used for bone fragment fixation, according to aspects of the present disclosure.
Figure 13B:
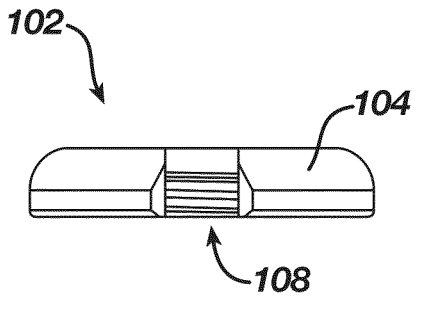
Figure 13C:
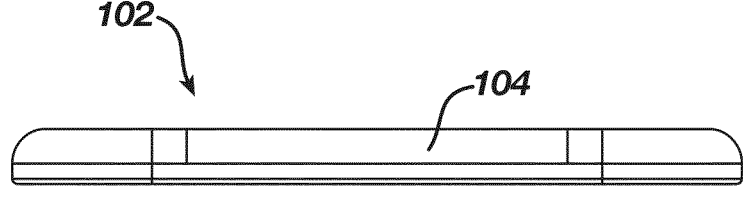

FIGS. 13A-13C, 14A-14C, 15A-15C, and 16A-16C provide different examples of an apparatus 102 that may be used for bone fragment fixation, as discussed herein. FIGS. 13A-13C show an example apparatus 102 including a plate 104 and three fixation holes 106. The fixation hole(s) 106 may include a first fixation hole 106a having a slot 108 disposed on an end of the plate 104 (as particularly shown in FIG. 13B), and two second fixation holes 106b fully enclosed within the plate 104.

Figure 14A:
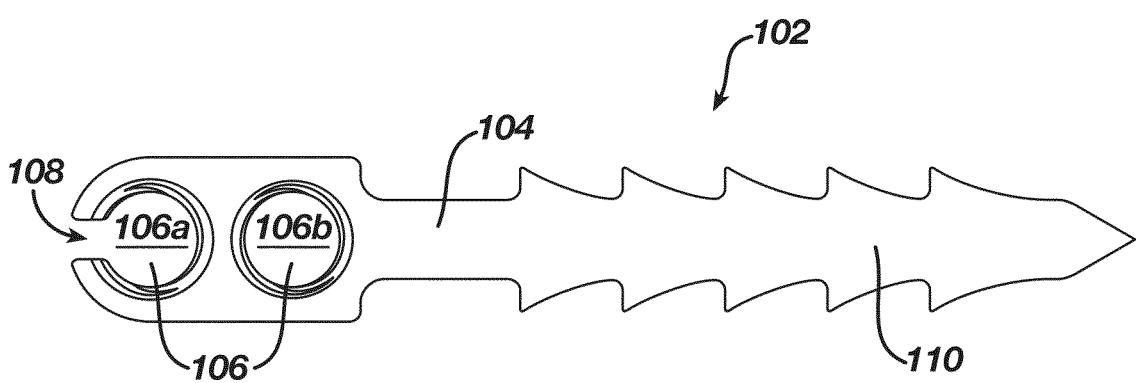
FIGS. 14A-14C provide top (A), end (B), and side (C) views of an example apparatus used for bone fragment fixation, according to aspects of the present disclosure.
Figure 14B:
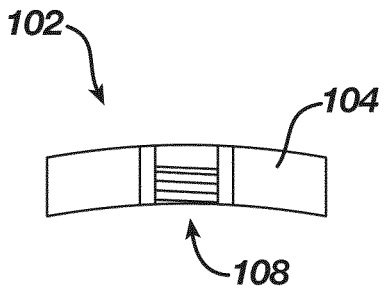
Figure 14C:
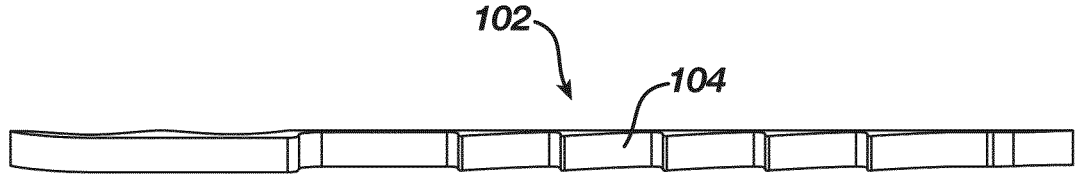

FIGS. 14A-14C show an example apparatus 102 including a plate 104 and two fixation holes 106. The fixation hole(s) 106 may include a first fixation hole 106a having a slot 108 disposed on an end of the plate 104 (as particularly shown in FIG. 14B), and one second fixation hole 106b fully enclosed within the plate 104. The apparatus 102 may further include an extension 110 that may be configured to be delivered intramedullary into the first bone 10, which may provide for added support when securing apparatus 102 onto the first bone 10.

Figure 15A:
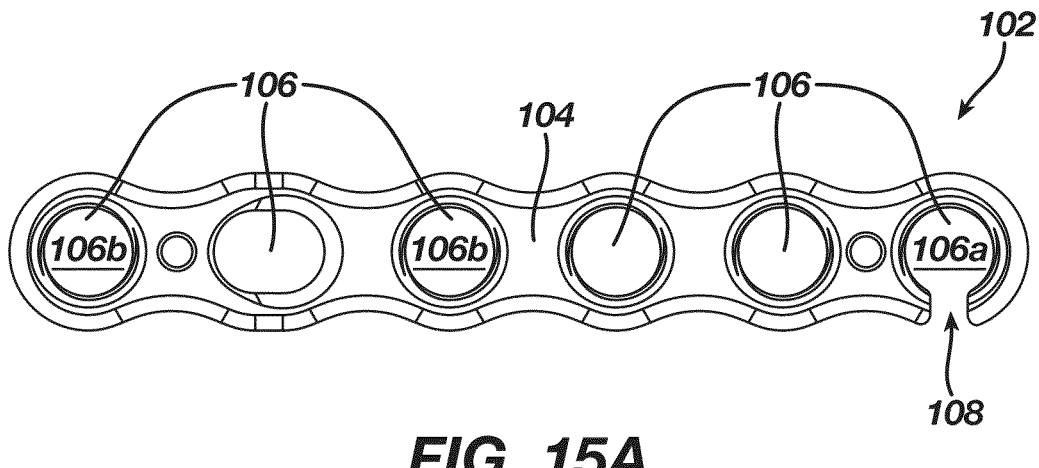
FIGS. 15A-15C provide top (A), end (B), and side (C) views of an example apparatus used for bone fragment fixation, according to aspects of the present disclosure.
Figure 15B:
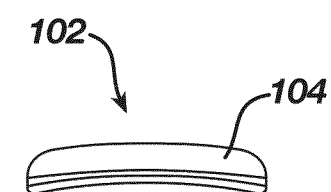
Figure 15C:
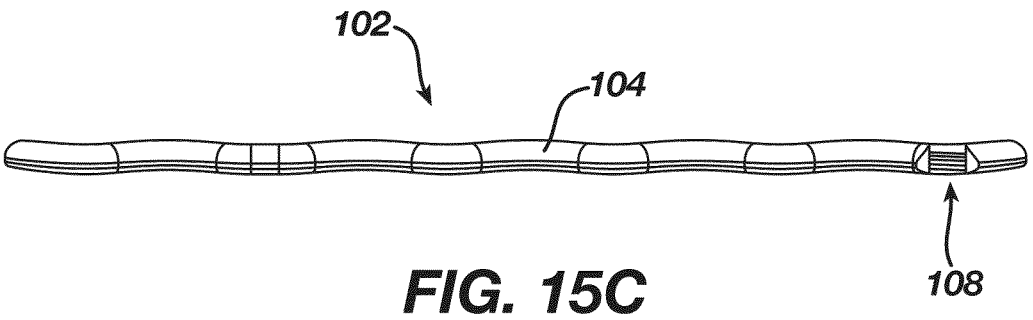

FIGS. 15A-15C show an example apparatus 102 including a plate 104 and six fixation holes 106. The fixation hole(s) 106 may include a first fixation hole 106a having a slot 108 disposed on a side of the plate 104 (as particularly shown in FIG. 15C), and five second fixation holes 106b fully enclosed within the plate 104.

Figure 16A:
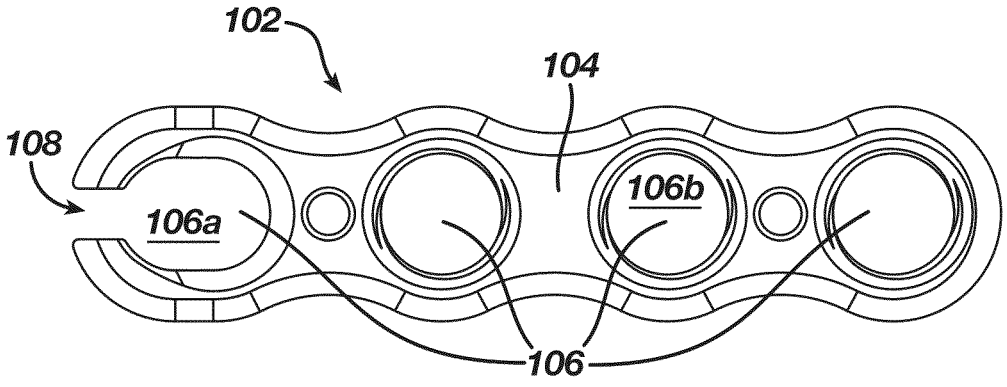
FIGS. 16A-16C provide top (A), end (B), and side (C) views of an example apparatus used for bone fragment fixation, according to aspects of the present disclosure.
Figure 16B:
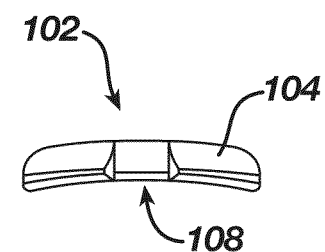
Figure 16C:
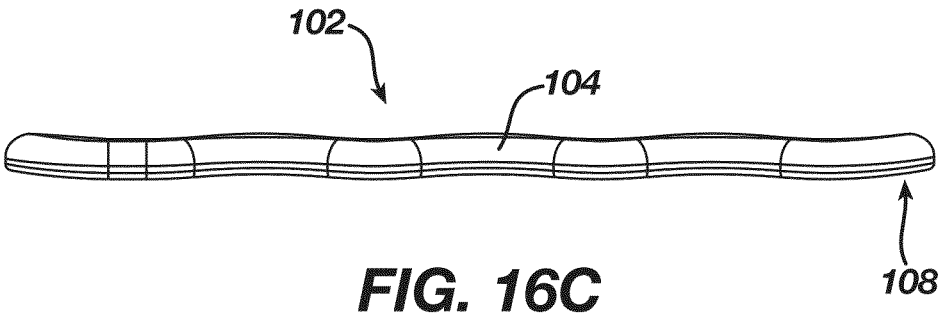

FIGS. 16A-16C show an example apparatus 102 including a plate 104 and four fixation holes 106. The fixation hole(s) 106 may include a first fixation hole 106a having a slot 108 disposed on an end of the plate 104 (as particularly shown in FIG. 16B), and three second fixation holes 106b fully enclosed within the plate 104.

FIG. 17 is a flowchart of a method 200 for bone fragment fixation. The steps of method 200 may be performed by one or more devices or components discussed herein (e.g., apparatus 102, first device 18, etc.). It should be understood that certain embodiments of the disclosed technology may omit one or more blocks as being optional.

In step 202, the method may include delivering a first device (e.g., first device 18) into a first bone (e.g., first bone 10) such that a first portion (e.g., 18a) of the first device is fixed in the first bone and a second portion (e.g., 18b) of the first device extends outward from the first bone. As discussed here, in some embodiments, the first device may be a K-wire.

In step 204, the method may include cutting the first bone to generate the bone fragment. The first portion of the first device may be fixed in the bone fragment (e.g., bone fragment 16). That is, as discussed herein, the first device may extend outward from the bone fragment such that a user, e.g., a surgeon, may easily manipulate or position the bone fragment using the first device. Step 204 may be performed after step 202.

In step 206, the method may include placing an apparatus (e.g., apparatus 102) on an exterior surface of the bone fragment. The apparatus may include two or more fixation holes, where at least a first fixation hole includes a slot (e.g., slot 108). Step 206 may be performed after step 204.

In step 208, the method may include positioning the second portion of the first device through the slot of the first fixation hole. As discussed herein, this step may allow a surgeon to align the bone fragment to anatomically normal conditions, such as a pre-fracture or pre-injury condition, or a typical anatomical condition for the bone or body part at issue. Step 208 may be performed after step 206.

In step 210, the method may include securing the apparatus onto the exterior surface of the bone fragment by delivering a first fixation device (e.g., a screw) into the bone fragment through a second fixation hole of the two or more fixation holes. Step 210 may be performed after step 208.

In step 212, the method may include removing the first device from the first bone. In some embodiments, a second fixation device (e.g., a second screw) may then be inserted into the first fixation hole, helping to further secure the apparatus onto the exterior surface of the bone fragment. Step 212 may be performed after step 210.

FIG. 18 is a flowchart of a method 300 for bone fragment fixation. The steps of method 300 may be performed by one or more devices or components discussed herein (e.g., apparatus 102, first device 18, etc.). It should be understood that certain embodiments of the disclosed technology may omit one or more blocks as being optional.

In step 302, the method may include delivering a first device (e.g., first device 18) into a first bone (e.g., first bone 10) such that a first portion (e.g., 18a) of the first device is fixed in the first bone and a second portion (e.g., 18b) and a third portion (e.g., 18c) of the first device extend outward from the first bone. As discussed here, in some embodiments, the first device may be a snap-off screw.

In step 304, the method may include cutting the first bone to generate the bone fragment. The first portion of the first device may be fixed in the bone fragment. That is, as discussed herein, the first device may extend outward from the bone fragment such that a user, e.g., a surgeon, may easily manipulate or position the bone fragment using the first device. Step 304 may be performed after step 302.

In step 306, the method may include placing an apparatus (e.g., apparatus 102) on an exterior surface of the bone fragment. The apparatus may include one or more fixation holes, where at least a first fixation hole includes a slot (e.g., slot 108). Step 306 may be performed after step 304.

In step 308, the method may include positioning the second and third portions of the first device through the slot of the first fixation hole. As discussed herein, this step may allow a surgeon to align the bone fragment to anatomically normal conditions, such as a pre-fracture or pre-injury condition, or a typical anatomical condition for the bone or body part at issue. Step 308 may be performed after step 306.

In step 310, the method may include inserting the third portion of the first device into the first bone, thereby securing the apparatus on the exterior surface of the bone fragment. For example, the first portion of the first device (e.g., the screw 26) may be fully inserted into the bone fragment until a screw head (e.g., screw head 30) of the first device sits flush with the exterior surface of the bone fragment. The delivery device may then be used to help "snap off" the second portion of the first device (e.g., the stem 28), leaving behind the screw 26 and screw head 30 to secure the apparatus to the bone fragment. Step 310 may be performed after step 308.

The descriptions contained herein are examples of embodiments of the disclosure and are not intended in any way to limit the scope of the disclosure. As described herein, the disclosure contemplates many variations and modifications of structures and methods, including alternative materials, alternative configurations of component parts, and alternative method steps. Modifications and variations apparent to those having skill in the pertinent art according to the teachings of this disclosure are intended to be within the scope of the claims which follow.

The disclosed technology described herein can be further understood according to the following clauses.

Clause 1: A method for fixating a bone fragment, the method comprising: delivering a first device into a first bone such that a first portion of the first device is fixed in the first bone and a second portion of the first device extends outward from the first bone; cutting the first bone to generate the bone fragment, wherein the first portion of the first device is fixed in the bone fragment; placing an apparatus on an exterior surface of the bone fragment, wherein the apparatus comprises two or more fixation holes, and wherein at least a first fixation hole of the two or more fixation holes comprises a slot; positioning the second portion of the first device through the slot of the first fixation hole; securing the apparatus onto the exterior surface of the bone fragment by delivering a first fixation device into the bone fragment through a second fixation hole of the two or more fixation holes; and removing the first device from the first bone.

Clause 2: The method of clause 1, wherein the first device comprises a Kirschner wire.

Clause 3: The method of any of clauses 1-2, further comprising: after removing the first device from the first bone, delivering a second fixation device into the bone fragment through the first fixation hole.

Clause 4: The method of clause 3, wherein the second fixation device comprises a screw.

Clause 5: The method of any of clauses 1-4, wherein the apparatus comprises a plate.

Clause 6: The method of clause 5, wherein the plate is planar.

Clause 7: The method of any of clauses 1-6, wherein the apparatus further comprises an extension configured to be delivered intramedullary to the first bone.

Clause 8: The method of any of clauses 1-7, wherein the slot is disposed on an end of the apparatus.

Clause 9: The method of any of clauses 1-7, wherein the slot is disposed on a side of the apparatus.

Clause 10: The method of any of clauses 1-9, wherein removing the first device from the first bone is performed after delivering the first fixation device into the bone fragment.

Clause 11: A method for fixating a bone fragment, the method comprising: delivering a first device into a first bone such that a first portion of the first device is fixed in the first bone and a second portion and a third portion of the first device extend outward from the first bone; cutting the first bone to generate the bone fragment, wherein the first portion of the first device is fixed in the bone fragment; placing an apparatus on an exterior surface of the bone fragment, wherein the apparatus comprises one or more fixation holes, and wherein at least a first fixation hole of the one or more fixation holes comprises a slot; positioning the second and third portions of the first device through the slot of the first fixation hole; and after positioning the second and third portions of the first device through the slot of the first fixation hole, inserting the third portion of the first device into the first bone thereby securing the apparatus on the exterior surface of the bone fragment.

Clause 12: The method of clause 11, wherein the first device comprises a snap-off screw.

Clause 13: The method of any of clauses 11-12, wherein: the first portion of the first device comprises a first section of a screw, the second portion of the first device comprises a stem, and the third portion of the first device comprises a second section of the screw.

Clause 14: The method of any of clauses 11-13, wherein the one or more fixation holes comprise two or more fixation holes, and the method further comprising: delivering a fixation device into the bone fragment through a second fixation hole of the two or more fixation holes.

Clause 15: The method of clause 14, wherein the fixation device comprise a screw.

Clause 16: The method of any of clauses 11-15, wherein cutting the first bone to generate the bone fragment is performed after delivering the first device into the first bone.

Clause 17: An apparatus for fixating a bone fragment of a first bone, the apparatus comprising: a plate; and one or more fixation holes, wherein a first fixation hole of the one or more fixation holes comprises a slot.

Clause 18: The apparatus of clause 17, wherein the plate is planar.

Clause 19: The apparatus of any of clauses 17-18, wherein the one or more fixation holes comprise two or more fixation holes, and wherein one or more second fixation holes of the two or more fixation holes are fully enclosed within the plate.

Clause 20: The apparatus of any of clauses 17-19, wherein the plate is configured to be secured onto an exterior surface of the bone fragment, and wherein the apparatus further comprises an extension configured to be delivered intramedullary to the first bone.

What is claimed is:

1. A method for fixating a bone fragment, the method comprising:
    delivering a first device into a first bone;
    cutting the first bone to generate the bone fragment such that a first portion of the first device is fixed in the bone fragment and a second portion of the first device extends outward from the bone fragment;
    placing an apparatus on an exterior surface of the bone fragment such that the first device is free from engagement with the apparatus, wherein the apparatus comprises two or more fixation holes, and wherein at least a first fixation hole of the two or more fixation holes comprises a slot;
    engaging the first device with the apparatus by moving the second portion of the first device around a portion of an outer perimeter of the apparatus, through the slot, and into the first fixation hole such that the second portion of the first device extends outward from the first fixation hole;
    securing the apparatus onto the exterior surface of the bone fragment by delivering a first fixation device into the bone fragment through a second fixation hole of the two or more fixation holes; and
    removing the first device from the first bone.

2. The method of claim 1, wherein the first device comprises a Kirschner wire.

3. The method of claim 1, further comprising:
    after removing the first device from the first bone, delivering a second fixation device into the bone fragment through the first fixation hole.

4. The method of claim 3, wherein the second fixation device comprises a screw.

5. The method of claim 1, wherein the apparatus comprises a planar plate.

6. The method of claim 5, wherein the apparatus further comprises an extension configured to be delivered intramedullary to the first bone.

7. The method of claim 1, wherein the slot is disposed on an outer-most end of the apparatus.

8. The method of claim 1, wherein the slot is disposed on a side of the apparatus.

9. The method of claim 1, wherein removing the first device from the first bone is performed after delivering the first fixation device into the bone fragment.

10. The method of claim 1, wherein cutting the first bone to generate the bone fragment is performed after delivering the first device into the first bone.

11. The method of claim 1, wherein placing the apparatus on the exterior surface of the bone fragment comprises placing a proximal-most end of the apparatus on the exterior surface of the bone fragment, and wherein the two or more fixation holes are disposed on the proximal-most end of the apparatus.

12. The method of claim 1, wherein placing the apparatus on the exterior surface of the bone fragment such that the first device is free from engagement with the apparatus comprises placing the apparatus on the exterior surface of the bone fragment such that the first device is disposed outside of the two or more fixation holes.

13. The method of claim 1, wherein the first fixation device is delivered into the bone fragment through the second fixation hole such that the first fixation device is fixed in the bone fragment approximately parallel to the first portion of the first device.

14. A method for fixating a bone fragment, the method comprising:

delivering a first device into a first bone;
  cutting the first bone to generate the bone fragment such that a first portion of the first device is fixed in the bone fragment and a second portion and a third portion of the first device extend outward from the bone fragment;

placing an apparatus on an exterior surface of the bone fragment such that the first device is free from engagement with the apparatus, wherein the apparatus comprises one or more fixation holes, and wherein at least a first fixation hole of the one or more fixation holes comprises a slot;

engaging the first device with the apparatus by moving the second and third portions of the first device around a portion of an outer perimeter of the apparatus, through the slot, and into the first fixation hole such that the second and third portions of the first device extend outward from the first fixation hole; and after positioning the second and third portions of the first device through the slot of the first fixation hole, inserting the third portion of the first device into the first bone thereby securing the apparatus on the exterior surface of the bone fragment.

15. The method of claim 14, wherein:

the first portion of the first device comprises a first section of a snap-off screw, the second portion of the first device comprises a stem of the snap-off screw, and the third portion of the first device comprises a second section of the snap-off screw.

16. The method of claim 14, wherein the one or more fixation holes comprise two or more fixation holes, and the method further comprising:

delivering a fixation device into the bone fragment through a second fixation hole of the two or more fixation holes.

* * * * *